(12) United States Patent
Nakagawa et al.

(10) Patent No.: US 10,090,163 B2
(45) Date of Patent: Oct. 2, 2018

(54) INORGANIC FILM-FORMING COMPOSITION FOR MULTILAYER RESIST PROCESSES, AND PATTERN-FORMING METHOD

(71) Applicant: JSR CORPORATION, Tokyo (JP)

(72) Inventors: Hisashi Nakagawa, Tokyo (JP); Tatsuya Sakai, Tokyo (JP); Shunsuke Kurita, Tokyo (JP); Satoshi Dei, Tokyo (JP); Kazunori Takanashi, Tokyo (JP); Yoshio Takimoto, Tokyo (JP); Masayuki Motonari, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/833,718

(22) Filed: Aug. 24, 2015

(65) Prior Publication Data

US 2015/0364332 A1    Dec. 17, 2015

Related U.S. Application Data

(63) Continuation of application No. PCT/JP2014/053821, filed on Feb. 18, 2014.

(30) Foreign Application Priority Data

Mar. 25, 2013 (JP) ................. 2013-063096

(51) Int. Cl.
| | |
|---|---|
| *H01L 21/308* | (2006.01) |
| *H01L 21/033* | (2006.01) |
| *G03F 7/11* | (2006.01) |
| *G03F 7/09* | (2006.01) |
| *G03F 7/36* | (2006.01) |
| *G03F 7/32* | (2006.01) |
| *G03F 7/20* | (2006.01) |
| *G03F 7/038* | (2006.01) |
| *G03F 7/039* | (2006.01) |
| *C07F 13/00* | (2006.01) |
| *C07F 11/00* | (2006.01) |
| *C07F 9/00* | (2006.01) |
| *C07F 7/28* | (2006.01) |
| *C07F 5/06* | (2006.01) |
| *C07F 5/00* | (2006.01) |

(52) U.S. Cl.
CPC ............ *H01L 21/3081* (2013.01); *C07F 5/00* (2013.01); *C07F 5/003* (2013.01); *C07F 5/06* (2013.01); *C07F 7/28* (2013.01); *C07F 9/00* (2013.01); *C07F 11/00* (2013.01); *C07F 13/00* (2013.01); *G03F 7/038* (2013.01); *G03F 7/039* (2013.01); *G03F 7/0382* (2013.01); *G03F 7/0392* (2013.01); *G03F 7/09* (2013.01); *G03F 7/094* (2013.01); *G03F 7/11* (2013.01); *G03F 7/2041* (2013.01); *G03F 7/322* (2013.01); *G03F 7/325* (2013.01); *G03F 7/36* (2013.01); *H01L 21/0332* (2013.01)

(58) Field of Classification Search
None
See application file for complete search history.

(56) References Cited

U.S. PATENT DOCUMENTS

| | | | | |
|---|---|---|---|---|
| 5,286,774 | A * | 2/1994 | McGibbon | C09D 11/10 524/382 |
| 2004/0043210 | A1* | 3/2004 | Seto | G02B 1/105 428/331 |
| 2008/0220343 | A1* | 9/2008 | Chen | G03F 7/0007 430/7 |
| 2009/0010636 | A1* | 1/2009 | Yamada | G03B 13/16 396/384 |
| 2010/0239984 | A1* | 9/2010 | Tsubaki | G03F 7/0392 430/325 |
| 2012/0148809 | A1* | 6/2012 | Kobayashi | B82Y 10/00 428/195.1 |

(Continued)

FOREIGN PATENT DOCUMENTS

| | | | |
|---|---|---|---|
| JP | 11-258813 | * | 9/1999 |
| JP | 2001-166490 A | | 6/2001 |
| JP | 2001-284209 A | | 10/2001 |

(Continued)

OTHER PUBLICATIONS

JPO English abstract for JP11-258813 (1999).*

(Continued)

*Primary Examiner* — Sin J Lee
(74) *Attorney, Agent, or Firm* — Oblon, McClelland, Maier & Neustadt, L.L.P.

(57) ABSTRACT

An inorganic film-forming composition for multilayer resist processes includes a complex that includes: metal atoms; at least one bridging ligand; and a ligand which is other than the at least one bridging ligand and which is derived from a hydroxy acid ester, a β-diketone, a β-keto ester, a β-dicarboxylic acid ester or a combination thereof. The at least one bridging ligand includes a first bridging ligand derived from a compound represented by formula (1). An amount of the first bridging ligand is no less than 50 mol % with respect to a total of the bridging ligand. In the formula (1), $R^1$ represents an organic group having a valency of n. X represents —OH, —COOH, —NCO or —NHR$^a$, wherein R$^a$ represents a hydrogen atom or a monovalent organic group. n is an integer of 2 to 4.

$$R^1\!-\!(X)_n \qquad (1)$$

18 Claims, No Drawings

(56) References Cited

U.S. PATENT DOCUMENTS

2012/0270994 A1* 10/2012 Kim .................. G03F 7/091
 524/553
2014/0193975 A1* 7/2014 Ogihara .............. C08G 77/58
 438/702

FOREIGN PATENT DOCUMENTS

| | | | |
|---|---|---|---|
| JP | 2002-182006 A | | 6/2002 |
| JP | 2003-297823 | * | 10/2003 |
| JP | 2005-173552 A | | 6/2005 |
| JP | 2005-537502 A | | 12/2005 |
| JP | 2008-039811 A | | 2/2008 |
| JP | 2010-085893 A | | 4/2010 |
| JP | 2010-085912 A | | 4/2010 |
| JP | 2012-215878 A | | 11/2012 |
| JP | 2014-134592 A | | 7/2014 |
| TW | 201432387 A | | 8/2014 |
| WO | WO 2004/001502 A1 | | 12/2003 |
| WO | WO 2011/024673 A1 | | 3/2011 |

OTHER PUBLICATIONS

Machine-assisted English translation for JP11-258813, provided by JPO (1999).*
Partial English translation of JP 2003-297823 (2003) provided by USPTO.*
Derwent English abstract for JP2003-297823 (2003).*
Machine-assisted English translation of JP 2003-297823 (2003) provided by JPO.*
International Search Report dated May 27, 2014 in PCT/JP2014/053821 filed Feb. 18, 2014 (w/ English translation).
Japanese Office Action dated Jul. 25, 2017 in Patent Application No. 2015-508171 (with English Translation).
Combined Office Action and Search Report dated Jul. 10, 2017 in Taiwan Patent Application No. 103110666 (with English translation).
Combined Office Action and Search Report dated Mar. 1, 2017 in Taiwanese Patent Application No. 103110666 (with English translation).

* cited by examiner

INORGANIC FILM-FORMING COMPOSITION FOR MULTILAYER RESIST PROCESSES, AND PATTERN-FORMING METHOD

CROSS-REFERENCE TO RELATED APPLICATIONS

The present application is a continuation application of International Application No. PCT/JP2014/053821, filed Feb. 18, 2014, which claims priority to Japanese Patent Application No. 2013-063096, filed Mar. 25, 2013. The contents of these applications are incorporated herein by reference in their entirety.

BACKGROUND OF THE INVENTION

Field of the Invention

The present invention relates to an inorganic film-forming composition for multilayer resist processes, and a pattern-forming method.

Discussion of the Background

Miniaturization of semiconductor devices and the like has been accompanied by the progress of a reduction in processing size by utilizing a multilayer resist process in order to achieve a higher degree of integration. In the multilayer resist process, an inorganic film is provided on a substrate using an inorganic film-forming composition, and then a resist pattern is formed on the inorganic film using an organic material that differs in etching rate from the inorganic film. Next, the resist pattern is transferred to the inorganic film by dry-etching, and further dry-etching is executed to transfer the pattern to the substrate, whereby a desired patterned substrate is obtained (see Japanese Unexamined Patent Application, Publication Nos. 2001-284209, 2010-85912, and 2008-39811). Recently, in addition to composition containing a silicon-containing compound, a composition has been investigated as the inorganic film-forming composition, which contains a metal-containing compound and can exhibit superior etching selectivity with respect to a silicon dioxide film provided adjacent to the inorganic film and also with respect to a resist underlayer film which is an organic film (see Japanese Unexamined Patent Application (Translation of PCT Application), Publication No. 2005-537502).

Such an inorganic film-forming composition is required to meet the following various characteristics. First, it is required that in forming a pattern, a coating film left after drying the composition can be removed through dissolution in a cleaning solvent used in an edge-and-back rinsing for cleaning the edge and the back face of the substrate. Moreover, the resulting inorganic film is required not only to be superior in the etching selectivity mentioned above, but also to enable a favorable shape of a resist pattern to be formed on the inorganic film. In addition, in order to achieve a sufficient antireflection effect in the multilayer resist process, it is reportedly preferred that the extinction coefficient of the inorganic film falls within a range of about 0.1 to about 0.5, and accordingly, the inorganic film-forming composition is also required to provide an inorganic film having such an extinction coefficient.

SUMMARY OF THE INVENTION

According to one aspect of the present invention, an inorganic film-forming composition for a multilayer resist process, includes a complex that includes: metal atoms; at least one bridging ligand; and another ligand which is other than the at least one bridging ligand and which is derived from a hydroxy acid ester, a β-diketone, a β-keto ester, a β-dicarboxylic acid ester or a combination thereof. The at least one bridging ligand includes a first bridging ligand derived from a compound represented by formula (1).

$$R^1\text{-}(X)_n \qquad (1)$$

In the formula (1), $R^1$ represents an organic group having a valency of n; X represents —OH, —COOH, —NCO or —NHR$^a$, wherein R$^a$ represents a hydrogen atom or a monovalent organic group; and n is an integer of 2 to 4, wherein a plurality of Xs are each identical or different. An amount of the first bridging ligand is no less than 50 mol % with respect to a total of the at least one bridging ligand.

According to another aspect of the present invention, an inorganic film-forming composition for a multilayer resist process, includes a product obtained in a reaction of: a metal compound that comprises two or more alkoxy ligands; a compound represented by formula (1); and a hydroxy acid ester, a β-diketone, a β-keto ester, a β-dicarboxylic acid ester, or a combination thereof.

$$R^1\text{-}(X)_n \qquad (1)$$

In the formula (1), $R^1$ represents an organic group having a valency of n; X represents —OH, —COOH, —NCO or —NHR$^a$, wherein R$^a$ represents a hydrogen atom or a monovalent organic group; and n is an integer of 2 to 4, wherein a plurality of Xs are each identical or different.

According to further aspect of the present invention, a pattern-forming method includes providing an inorganic film directly or indirectly on a substrate using the inorganic film-forming composition. A resist pattern is formed directly or indirectly on the inorganic film. A pattern id formed on the substrate by at least one dry-etching operation using the resist pattern as a mask.

DESCRIPTION OF THE EMBODIMENTS

According to an embodiment of the invention, an inorganic film-forming composition for multilayer resist processes contains a complex (hereinafter, may be also referred to as "(A) complex" or "complex (A)") that contains: a plurality of metal atoms; a bridging ligand; and (b) a ligand derived from at least one compound selected from the group consisting of a hydroxy acid ester, a β-diketone, a β-keto ester and a β-dicarboxylic acid ester, wherein the bridging ligand includes (a) a bridging ligand derived from a compound represented by the following formula (1), and the amount of the bridging ligand (a) is no less than 50 mol % with respect to a total of the bridging ligands, $$R^1\text{-}(X)_n \qquad (1)$$

wherein in the formula (1), $R^1$ represents an organic group having a valency of n; X represents —OH, —COOH, —NCO or —NHR$^a$, wherein R$^a$ represents a hydrogen atom or a monovalent organic group; and n is an integer of 2 to 4, wherein a plurality of Xs may be each identical or different.

According to another embodiment of the present invention, a pattern-forming method includes: providing an inorganic film directly or indirectly on a substrate (providing an inorganic film on an upper face side of a substrate); forming a resist pattern directly or indirectly on the inorganic film (i.e., forming a resist pattern on an upper face side of the inorganic film); and forming a pattern on the substrate by at least one dry-etching operations using the resist pattern as a mask, wherein the inorganic film is provided using the inorganic film-forming composition for multilayer resist processes according to the embodiment of the present invention.

The "organic group" as referred to herein means a group that includes at least one carbon atom.

According to the inorganic film-forming composition for multilayer resist processes and the pattern-forming method of the embodiments of the present invention, an inorganic film can be formed which has a small extinction coefficient and achieves superior resist pattern formability and etching selectivity while exhibiting superior removability by a cleaning solvent. Therefore, these can be highly suitably used in manufacture of LSIs in which further progress of miniaturization is expected in the future, in particular, for forming fine contact holes and the like. Hereinafter, embodiments of the present invention will be described in detail.

Inorganic Film-Forming Composition for Multilayer Resist Processes

In a multilayer resist process, more specifically, a process in which a substrate is processed through forming other layer(s) such as an organic underlayer film and an SOG (Spin on Glass) film in addition to the resist pattern, an inorganic film-forming composition for multilayer resist processes according to an embodiment of the present invention is used to provide an inorganic film as the other layer.

The inorganic film-forming composition for multilayer resist processes contains (A) a complex. The composition may contain as favorable components, a solvent (hereinafter, may be also referred to as "(B) solvent" or "solvent (B)"), and a crosslinking accelerator (hereinafter, may be also referred to as "(C) crosslinking accelerator" or "crosslinking accelerator (C)"), and may contain other optional component within a range not leading to impairment of the effects of the present invention. Hereinafter, each component will be explained.

(A) Complex

The complex (A) contains a plurality of metal atoms, a bridging ligand, and (b) a ligand, wherein the bridging ligand includes (a) a bridging ligand, and the amount of the bridging ligand (a) is no less than 50 mol % with respect to a total of the bridging ligands.

Due to containing the complex (A), the inorganic film-forming composition can form an inorganic film that is superior in removability by a cleaning solvent, has a small extinction coefficient and is also superior in resist pattern formability and etching selectivity.

Although not necessarily clarified, the reason for achieving the effects described above due to the inorganic film-forming composition for multilayer resist processes containing the complex (A) is presumed, for example, as in the following. Specifically, the complex (A) is a multinuclear complex that contains the bridging ligand (a) derived from the compound represented by the above formula (1), and the plurality of metal atoms. Moreover, since the amount of the bridging ligand (a) is no less than 50 mol % with respect to a total of the bridging ligands, it is presumed that the complex (A) would have a structure in which the metal atoms are bridged by way of not —O— or the like but principally the bridging ligand (a). Due to having such a structure, the complex (A) has an increased solubility in an organic solvent, and consequently the inorganic film-forming composition exhibits superior removability by a cleaning solvent. Moreover, it is presumed that since the complex (A) having such a multinuclear structure is used as a precursor, the inorganic film having a small extinction coefficient can be formed.

Hereinafter, the metal atom, the bridging ligand, the bridging ligand (a) and the ligand (b) which constitute the complex (A) will be explained in this order.

Metal Atom

The complex (A) contains a plurality of metal atoms. The plurality of metal atoms are believed to be bridged with the bridging ligand that includes the bridging ligand (a). Further, the ligand (b) coordinates to the plurality of metal atoms. Due to containing the plurality of metal atoms, the inorganic film-forming composition is superior in resist pattern formability and etching selectivity.

The metal atom is not particularly limited as long as it is an atom of a metal element, and examples thereof include atoms from:

Group 3 elements such as Sc (scandium) and Y (yttrium);

Group 4 elements such as Ti (titanium), Zr (zirconium) and Hf (hafnium);

Group 5 elements such as V (vanadium), Nb (niobium) and Ta (tantalum);

Group 6 elements such as Cr (chromium), Mo (molybdenum) and W (tungsten);

Group 12 elements such as Zn;

Group 13 elements such as Al (aluminum), Ga (gallium), In (indium) and Tl (thallium); and the like.

Of these, atoms of the Group 3 elements, the Group 4 elements, the Group 5 elements, the Group 6 elements or the Group 13 elements are preferred, and atoms of Y, Ti, Zr, Hf, Ta, W or Al are more preferred.

The lower limit of the average number of metal atoms contained in the complex (A) is preferably 5, more preferably 10, and still more preferably 15. The upper limit of the average number is preferably 100, more preferably 80, and still more preferably 60. When the average number of metal atoms falls within the above range, the extinction coefficient of the inorganic film formed from the inorganic film-forming composition can be adjusted more properly.

In light of achieving a smaller extinction coefficient of the inorganic film formed from the inorganic film-forming composition, the amount of the metal atom is preferably no less than 50 mol %, more preferably no less than 80 mol %, still more preferably no less than 95 mol %, and particularly preferably no less than 99 mol % with respect to a sum of the metal atoms and the metalloid atoms contained in the complex (A). The metal atoms may be contained either alone, or atoms of two or more types of elements may be contained.

Bridging Ligand

The complex (A) contains a bridging ligand. Due to containing the bridging ligand, the complex (A) can form a multinuclear complex. This bridging ligand is exemplified by an oxygen atom (—O—), a peroxide ligand (—O—O—), and the like, in addition to the bridging ligand (a) explained below. This bridging ligand typically coordinates so as to link the metal atoms.

Bridging Ligand (a)

The bridging ligand (a) is as described above, and derived from a compound represented by the following formula (1) (hereinafter, may be also referred to as "compound (A)"). The amount of the bridging ligand (a) is no less than 50 mol %, preferably no less than 70 mol %, more preferably no less than 90 mol %, and still more preferably no less than 95 mol % with respect to a total of the bridging ligands. Since the complex (A) contains the bridging ligand (a) as the bridging ligand, and the amount of the bridging ligand (a) with respect to a total of the bridging ligands falls within the above range, the complex (A) can form a multinuclear complex bridged principally with an organic ligand. As a result, the inorganic film-forming composition can exhibit superior removability by a cleaning solvent, and a small extinction coefficient of the inorganic film formed from the inorganic film-forming composition can be achieved. The bridging ligand (a) is exemplified by the compound (A) itself, an anion formed through elimination of a proton from the compound (A), and the like, and coordinates to the metal atoms via an oxygen atom and/or a nitrogen atom included therein.

  (1)

In the above formula (1), $R^1$ represents an organic group having a valency of n; X represents —OH, —COOH, —NCO or —NHR$^a$, wherein R$^a$ represents a hydrogen atom or a monovalent organic group; and n is an integer of 2 to 4, wherein a plurality of Xs may be each identical or different.

The organic group having a valency of n which is represented by $R^1$ is exemplified by: a hydrocarbon group having a valency of n; a hetero atom-containing group having a valency of n which is obtained from the hydrocarbon group by incorporating a hetero atom-including group between adjacent two carbons thereof; a group having a valency of n which is obtained by substituting a part or all of hydrogen atoms included in the hydrocarbon group or the hetero atom-containing group with a substituent; and the like.

Examples of the hydrocarbon group having a valency of n include groups obtained by eliminating n hydrogen atoms from hydrocarbons such as: chain hydrocarbons having 1 to 30 carbon atoms, e.g., alkanes such as methane, ethane, propane and butane; alkenes such as ethene, propene, butene and pentene, and alkynes such as ethyne, propyne, butyne and pentyne; alicyclic hydrocarbons having 3 to 30 carbon atoms, e.g., cycloalkane such as cyclopropane, cyclobutane, cyclopentane, cyclohexane, norbornane and adamantane, and cycloalkenes such as cyclopropene, cyclobutene, cyclopentene, cyclohexene and norbornene; aromatic hydrocarbons having 6 to 30 carbon atoms, e.g., arenes such as benzene, toluene, xylene, mesitylene, naphthalene, methylnaphthalene, dimethylnaphthalene and anthracene; and the like.

The hetero atom-including group is exemplified by a group that includes at least one selected from the group consisting of an oxygen atom, a nitrogen atom, a silicon atom, a phosphorus atom and a sulfur atom, and the like, and is further exemplified by —O—, —NH—, —CO—, —S—, a combination thereof, and the like. Of these, —O— is preferred.

Examples of the substituent include:
halogen atoms such as a fluorine atom, a chlorine atom, a bromine atom and an iodine atom;
alkoxy groups such as a methoxy group, an ethoxy group and a propoxy group;
alkoxycarbonyl groups such as a methoxycarbonyl group and an ethoxycarbonyl group;
alkoxycarbonyloxy groups such as a methoxycarbonyloxy group and an ethoxycarbonyloxy group;
acyl groups such as a formyl group, an acetyl group, a propionyl group, a butyryl group and a benzoyl group;
a cyano group and a nitro group; and the like.

Preferably, n is 2 or 3, and more preferably 2.

The monovalent organic group represented by R$^a$ in —NHR$^a$ is exemplified by: a monovalent hydrocarbon group having 1 to 20 carbon atoms; a hetero atom-containing group obtained from the hydrocarbon group by incorporating a hetero atom-including group between adjacent two carbons thereof; a group obtained by substituting a part or all of hydrogen atoms included in the hydrocarbon group or the hetero atom-containing group with a substituent; and the like. R$^a$ represents preferably a monovalent hydrocarbon group, more preferably a monovalent chain hydrocarbon group, still more preferably an alkyl group, and particularly preferably a methyl group.

When n is 2, $R^1$ represents preferably a divalent chain hydrocarbon group, a divalent aromatic hydrocarbon group, or a divalent hetero atom-containing group, more preferably an alkanediyl group, an alkenediyl group, an arenediyl group, or an alkanediyloxyalkanediyl group, and still more preferably a 1,2-ethanediyl group, a 1,2-propanediyl group, a butanediyl group, a hexanediyl group, an ethenediyl group, a xylenediyl group, an ethanediyloxyethanediyl group.

When n is 3, $R^1$ represents preferably a trivalent chain hydrocarbon group, more preferably an alkanetriyl group, and still more preferably a 1,2,3-propanetriyl group.

When n is 4, $R^1$ represents preferably a tetravalent chain hydrocarbon group, more preferably an alkanetetrayl group, and still more preferably a 1,2,3,4-butanetetrayl group.

Examples of the compound (A) include compounds represented by the following formulae (1-1) to (1-4) (hereinafter, may be also referred to as "compounds (1-1) to (1-4)"), and the like.

  (1-1)

  (1-2)

  (1-3)

  (1-4)

In the above formulae (1-1) to (1-4), $R^1$, $R^a$, $R^b$ and n are as defined in the above formula (1).

When n is 2, examples of the compound (1-1) include:
alkylene glycols such as ethylene glycol, propylene glycol, butylene glycol and hexamethylene glycol;
dialkylene glycols such as diethylene glycol, dipropylene glycol, dibutylene glycol, triethylene glycol and tripropylene glycol;
cycloalkylene glycols such as cyclohexanediol, cyclohexanedimethanol, norbornanediol, norbornanedimethanol and adamantanediol;
aromatic ring-containing glycols such as 1,4-benzenedimethanol and 2,6-naphthalenedimethanol;
dihydric phenols such as catechol, resorcinol and hydroquinone; and the like.

When n is 3, examples of the compound (1-1) include:
alkanetriols such as glycerin and 1,2,4-butanetriol;
cycloalkanetriols such as 1,2,4-cyclohexanetriol and 1,2,4-cyclohexanetrimethanol;
aromatic ring-containing glycols such as 1,2,4-benzenetrimethanol and 2,3,6-naphthalenetrimethanol;
trihydric phenols such as pyrogallol and 2,3,6-naphthalenetriol; and the like.

When n is 4, examples of the compound (1-1) include:
alkanetetraols such as erythritol and pentaerythritol;
cycloalkanetetraols such as 1,2,4,5-cyclohexanetetraol;
aromatic ring-containing tetraols such as 1,2,4,5-benzenetetramethanol;
tetrahydric phenols such as 1,2,4,5-benzenetetraol; and the like.

Of these, the compounds (1-1) wherein n is 2 or 3 are preferred, alkylene glycols, dialkylene glycols and alkanetriols are more preferred, and propylene glycol, diethylene glycol and glycerin are still more preferred.

When n is 2, examples of the compound (1-2) include:
chain saturated dicarboxylic acids such as oxalic acid, malonic acid, succinic acid, glutaric acid and adipic acid;
chain unsaturated dicarboxylic acids such as maleic acid and fumaric acid;
alicyclic dicarboxylic acids such as 1,4-cyclohexanedicarboxylic acid, norbornanedicarboxylic acid and adamantanedicarboxylic acid;
aromatic dicarboxylic acids such as phthalic acid, terephthalic acid, 2,6-naphthalenedicarboxylic acid and 2,7-naphthalenedicarboxylic acid; and the like.

When n is 3, examples of the compound (1-2) include:
chain saturated tricarboxylic acids such as 1,2,3-propanetricarboxylic acid;
chain unsaturated tricarboxylic acids such as 1,2,3-propenetricarboxylic acid;
alicyclic tricarboxylic acids such as 1,2,4-cyclohexanetricarboxylic acid;
aromatic tricarboxylic acids such as trimellitic acid and 2,3,7-naphthalenetricarboxylic acid; and the like.

When n is 4, examples of the compound (1-2) include:
chain saturated tetracarboxylic acids such as 1,2,3,4-butanetetracarboxylic acid;
chain unsaturated tetracarboxylic acids such as 1,2,3,4-butadienetetracarboxylic acid;
alicyclic tetracarboxylic acids such as 1,2,5,6-cyclohexanetetracarboxylic acid and 2,3,5,6-norbornanetetracarboxylic acid;
aromatic tetracarboxylic acids such as pyromellitic acid and 2,3,6,7-naphthalenetetracarboxylic acid; and the like.

Of these, the compounds (1-2) wherein n is 2 are preferred, chain saturated dicarboxylic acids and chain unsaturated dicarboxylic acids are more preferred, and maleic acid and succinic acid are still more preferred.

When n is 2, examples of the compound (1-3) include:
chain diisocyanates such as ethylene diisocyanate, trimethylene diisocyanate, tetramethylene diisocyanate and hexamethylene diisocyanate;
alicyclic diisocyanates such as 1,4-cyclohexane diisocyanate and isophorone diisocyanate;
aromatic diisocyanates such as tolylene diisocyanate, 1,4-benzene diisocyanate and 4,4'-diphenylmethane diisocyanate; and the like.

When n is 3, examples of the compound (1-3) include:
chain triisocyanates such as trimethylene triisocyanate;
alicyclic triisocyanates such as 1,2,4-cyclohexane triisocyanate;
aromatic triisocyanates such as 1,2,4-benzene triisocyanate; and the like.

When n is 4, examples of the compound (1-3) include:
chain tetraisocyanates such as tetramethylene tetraisocyanate;
alicyclic tetraisocyanates such as 1,2,4,5-cyclohexane tetraisocyanate;
aromatic tetraisocyanates such as 1,2,4,5-benzene tetraisocyanate; and the like.

Of these, the compounds (1-3) wherein n is 2 are preferred, chain diisocyanates are more preferred, and hexamethylene diisocyanate is still more preferred.

When n is 2, examples of the compound (1-4) include:
chain diamines such as ethylenediamine, N-methylethylenediamine, N,N'-dimethylethylenediamine, trimethylenediamine, N,N'-dimethyltrimethylenediamine, tetramethylenediamine, and N,N'-dimethyltetramethylenediamine;
alicyclic diamines such as 1,4-cyclohexanediamine and 1,4-di(aminomethyl)cyclohexane;
aromatic diamines such as 1,4-diaminobenzene and 4,4'-diaminodiphenylmethane; and the like.

When n is 3, examples of the compound (1-4) include:
chain triamines such as triaminopropane and N,N',N''-trimethyltriaminopropane;
alicyclic triamines such as 1,2,4-triaminocyclohexane;
aromatic triamines such as 1,2,4-triaminobenzene; and the like.

When n is 4, examples of the compound (1-4) include:
chain tetraamines such as tetraaminobutane;
alicyclic tetraamines such as 1,2,4,5-tetraaminocyclohexane, 2,3,5,6-tetraaminonorbornane;
aromatic tetraamines such as 1,2,4,5-tetraaminobenzene; and the like.

Of these, the compounds (1-4) wherein n is 2 are preferred, chain diamines are more preferred, and N,N'-dimethylethylenediamine is still more preferred.

Ligand (b)

The ligand (b) is a ligand derived from at least one compound selected from the group consisting of a hydroxy acid ester, a β-diketone, a β-keto ester and a β-dicarboxylic acid ester, and coordinates to the metal atoms of the complex (A). Due to the complex (A) containing the ligand (b) in addition to the bridging ligand (a), the solubility of the complex (A) in an organic solvent can be increased. Consequently, the inorganic film-forming composition can exhibit superior removability by a cleaning solvent. The ligand (b) coordinates to the metal atoms typically through the binding of two or more oxygen atoms included in the ligand (b) to a plurality of coordination sites of the metal atoms.

The hydroxy acid ester is not particularly limited as long as it is a carboxylic acid ester that includes a hydroxy group, and examples thereof include a compound represented by the following formula (2), and the like.

In the above formula (2), $R^A$ represents a divalent organic group having 1 to 20 carbon atoms; and $R^B$ represents a monovalent organic group having 1 to 20 carbon atoms.

Examples of the divalent organic group represented by $R^A$ include organic groups having the valency of n of 2 and having 1 to 20 carbon atoms, and the like among the organic groups exemplified in connection with $R^1$ in the above formula (1). Examples of the monovalent organic group represented by $R^B$ include monovalent organic groups similar to those exemplified in connection with the monovalent organic group represented by $R^a$ in the above formula (1), and the like.

Examples of the hydroxy acid ester include glycolic acid esters, lactic acid esters, 2-hydroxycyclohexane-1-carboxylic acid esters, salicylic acid esters, and the like. Of these, lactic acid esters are preferred, and ethyl lactate is more preferred.

The β-diketone is not particularly limited as long as it has a 1,3-diketo structure, and examples thereof include a compound represented by the following formula (3), and the like.

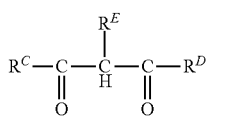

(3)

In the above formula (3), $R^C$ and $R^D$ each independently represent a monovalent organic group having 1 to 20 carbon atoms; and $R^E$ represents a hydrogen atom or a monovalent organic group having 1 to 20 carbon atoms.

Examples of the monovalent organic group having 1 to 20 carbon atoms represented by $R^B$, $R^C$ or $R^D$ include monovalent organic groups similar to those exemplified in connection with the monovalent organic group represented by $R^a$ in the above formula (1), and the like.

Examples of the β-diketone include acetylacetone, methylacetylacetone, ethylacetylacetone, 2,4-pentanedione, 3-methyl-2,4-pentanedione, and the like. Of these, acetylacetone is preferred.

The β-keto ester is not particularly limited as long as it is a carboxylic acid ester compound that includes a ketonic carbonyl group at a β-position thereof, and examples thereof include a compound represented by the following formula (4), and the like.

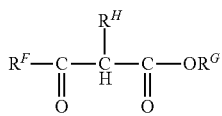

(4)

In the above formula (4), $R^F$ and $R^G$ each independently represent a monovalent organic group having 1 to 20 carbon atoms; and $R^H$ represents a hydrogen atom or a monovalent organic group having 1 to 20 carbon atoms.

Examples of the monovalent organic group having 1 to 20 carbon atoms which is represented by $R^F$, $R^G$ or $R^H$ include monovalent organic groups similar to those exemplified in connection with the monovalent organic group represented by $R^a$ in the above formula (1), and the like.

Examples of the β-keto ester include acetoacetic acid esters, α-alkyl-substituted acetoacetic acid esters, β-ketopentanoic acid esters, benzoylacetic acid esters, 1,3-acetonedicarboxylic acid diesters, and the like. Of these, acetoacetic acid esters and 1,3-acetonedicarboxylic acid diesters are preferred, and ethyl acetoacetate and diethyl 1,3-acetonedicarboxylate are more preferred.

The β-dicarboxylic acid ester is exemplified by a compound represented by the following formula (5), and the like.

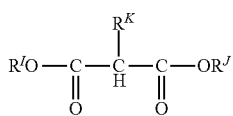

(5)

In the above formula (5), $R^I$ and $R^J$ each independently represent a monovalent organic group having 1 to 20 carbon atoms; and $R^K$ represents a hydrogen atom or a monovalent organic group having 1 to 20 carbon atoms.

Examples of the monovalent organic group having 1 to 20 carbon atoms represented by $R^I$, $R^J$ or $R^K$ include monovalent organic groups similar to those exemplified in connection with the monovalent organic group represented by $R^a$ in the above formula (1).

Examples of the β-dicarboxylic acid ester include malonic acid diesters, α-alkyl-substituted malonic acid diesters, α-cycloalkyl-substituted malonic acid diesters, α-aryl-substituted malonic acid diesters, and the like. Of these, malonic acid diesters are preferred, and diethyl malonate is more preferred.

The lower limit of the content of the ligand (b) with respect to the metal atoms (i.e., the number of moles of the ligand (b)/the number of moles of the metal atom) is preferably 10 mol %, more preferably 20 mol %, and still more preferably 30 mol %. The upper limit of the content of the ligand (b) with respect to the metal atoms is preferably 400 mol %, more preferably 350 mol %, and still more preferably 300 mol %. When the content of the ligand (b) with respect to the metal atoms falls within the above range, the removability by a cleaning solvent of the inorganic film-forming composition can be improved.

The bridging ligand (a) and the ligand (b) occupy preferably no less than 50%, more preferably no less than 60%, and still more preferably no less than 70% of coordination sites of the metal atoms. When the bridging ligand (a) and the ligand (b) occupy the coordination sites of the metal atoms in the proportion falling within the above range, the removability by a cleaning solvent of the inorganic film-forming composition can be further improved. It is to be noted that the number of coordination sites of the metal atoms in the complex (A) as referred to means a sum of the number of coordination sites on each metal atom. In addition, the occupancy rate of the coordination sites of the metal atoms means an average occupancy rate over the total metal atoms.

The lower limit of the number average molecular weight of the complex (A) is preferably 300, more preferably 500, and still more preferably 1,000. The upper limit of the number average molecular weight of the complex (A) is preferably 10,000, more preferably 9,000, and still more preferably 8,500. When the number average molecular weight of the complex (A) falls within the above range, the inorganic film-forming composition allows the extinction coefficient of the inorganic film formed from the inorganic film-forming composition to be adjusted more properly.

Synthesis Method of Complex (A)

The complex (A) can be obtained as a product of a reaction of, for example, a metal compound that includes two or more alkoxy ligands, the compound represented by the following formula (1), and at least one compound selected from the group consisting of a hydroxy acid ester, a β-diketone, a β-keto ester and a β-dicarboxylic acid ester in a solvent. In this example, a reaction of the metal compound that includes two or more alkoxy ligands with at least one ligand selected from the group consisting of a hydroxy acid ester, a β-diketone, a β-keto ester and a β-dicarboxylic acid ester may be allowed to proceed first to obtain a metal compound in which the ligand coordinates to the metal, and thereafter the metal compound thus obtained may be allowed to react with a compound represented by the following formula (1). Examples of the alkoxy ligand include a methoxide ligand, an ethoxide ligand, an isopropoxide ligand, a butoxide ligand, and the like. The metal compound may include a halide ligand such as a chloride ligand or a bromide ligand, and the like, in place of alkoxy ligand.

$$R^1\text{−}(\text{X})_n \quad (1)$$

In the above formula (1), $R^1$ represents an organic group having a valency of n; X represents —OH, —COOH, —NCO or —NHR$^a$, wherein R$^a$ represents a hydrogen atom or a monovalent organic group; and n is an integer of 2 to 4, wherein a plurality of Xs may be each identical or different.

The solvent for use in the aforementioned reaction is not particularly limited, and examples thereof include alcohol solvents, ketone solvents, amide solvents, ether solvents, ester solvents, hydrocarbon solvents, and the like. These solvents are exemplified by solvents exemplified in connection with the solvent (B) described later, and the like. Of these, alcohol solvents, ether solvents, ester solvents and hydrocarbon solvents are preferred, monovalent aliphatic alcohols, alkylene glycol monoalkyl ethers, hydroxy acid esters, alkylene glycol monoalkyl ether carboxylic acid esters, cyclic ethers and aromatic hydrocarbons are more preferred, monovalent aliphatic alcohols having 4 or more carbon atoms, alkylene glycol monoalkyl ethers having 6 or more carbon atoms, hydroxy acid esters having 4 or more carbon atoms, alkylene glycol monoalkyl ether carboxylic acid esters having 6 or more carbon atoms, cyclic ethers having 4 or more carbon atoms, and aromatic hydrocarbons having 7 or more carbon atoms are still more preferred, and butanol, propylene glycol monomethyl ether, propylene glycol monoethyl ether, propylene glycol monopropyl ether, ethyl lactate, propylene glycol monomethyl ether acetate, tetrahydrofuran and toluene are particularly preferred. After the completion of the reaction, the solvent used in the reaction may be used directly as the solvent (B) of the inorganic film-forming composition without removal.

The temperature of the reaction is preferably 0° C. to 150° C., and more preferably 10° C. to 120° C. The time period of the reaction is preferably 30 min to 24 hrs, more preferably 1 hour to 20 hrs, and still more preferably 2 hrs to 15 hrs.

The reaction is carried out in the presence of water in an amount of preferably no greater than 50 mol %, more preferably no greater than 30 mol %, and still more preferably no greater than 10 mol % with respect to the metal compound. When the reaction is carried out in the presence of water in the amount falling within the above range, the formation of a structure which includes —O— as the bridging ligand and which is formed upon a reaction of the metal compound with water can be reduced, and consequently the amount of the bridging ligand (a) with respect to a total of the bridging ligands in the complex (A) thus obtained can be increased. As a result, the removability by a cleaning solvent of the inorganic film-forming composition can be improved.

In the reaction product, preferably no less than 50 mol %, preferably no less than 70 mol % and preferably no less than 90 mol % of the alkoxy ligands contained in the metal compound is substituted. When the rate of substitution of the alkoxy ligands of the metal compound used in the reaction falls within the above range, the proportion of the occupation of the coordination sites of the metal atom by the bridging ligand (a) and the ligand (b) in the complex (A) thus obtained can be increased, and consequently the removability by a cleaning solvent of the inorganic film-forming composition can be improved.

(B) Solvent

The inorganic film-forming composition typically contains (B) a solvent. Any solvent can be used as the solvent (B) as long as it is capable of dissolving or dispersing the complex (A). The solvent (B) is exemplified by an alcohol solvent, a ketone solvent, an amide solvent, an ether solvent, an ester solvent, and the like. These solvents may be used either alone, or as a mixture of two or more types thereof. The solvent (B) may be the same as the compound giving the ligand (b) of the complex (A). Moreover, the solvent used in the reaction for the aforementioned synthesis of the complex (A) may be directly used as the solvent (B) without removal.

Examples of the alcohol solvent include:

monovalent aliphatic alcohols such as methanol, ethanol, n-propanol, iso-propanol, n-butanol, iso-butanol, sec-butanol, tert-butanol, n-pentanol, iso-amyl alcohol, 2-methylbutanol, sec-pentanol, tert-pentanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol and sec-heptadecyl alcohol;

monovalent alicyclic alcohols such as cyclohexanol, methylcyclohexanol and 3,3,5-trimethylcyclohexanol;

aromatic alcohols such as benzyl alcohol and phenethyl alcohol;

monovalent ether group- or keto group-containing alcohols such as 3-methoxybutanol, furfuryl alcohol and diacetone alcohol;

polyhydric alcohols such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

alkylene glycol monoalkyl ethers such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, propylene glycol monomethyl ether, propylene glycol monoethyl ether, propylene glycol monopropyl ether and propylene glycol monobutyl ether;

ether group-containing alkylene glycol monoalkyl ethers such as diethylene glycol monomethyl ether, diethylene glycol monoethyl ether, diethylene glycol monopropyl ether, diethylene glycol monobutyl ether, diethylene glycol monohexyl ether, dipropylene glycol monomethyl ether, dipropylene glycol monoethyl ether and dipropylene glycol monopropyl ether; and the like.

Examples of the ketone solvent include:

chain ketones such as acetone, methyl ethyl ketone, methyl n-propyl ketone, methyl n-butyl ketone, diethyl ketone, methyl iso-butyl ketone, methyl n-pentyl ketone, ethyl n-butyl ketone, methyl n-hexyl ketone, di-iso-butyl ketone and trimethylnonanone;

cyclic ketones such as cyclopentanone, cyclohexanone, cycloheptanone, cyclooctanone and methylcyclohexanone;

aromatic ketones such as acetophenone and phenyl ethyl ketone;

γ-diketones such as acetonyl acetone; and the like.

Examples of the amide solvent include:

chain amides such as N-methylformamide, N,N-dimethylformamide, N,N-diethylformamide, acetamide, N-methylacetamide, N,N-dimethylacetamide and N-methylpropionamide;

cyclic amides such as N-methylpyrrolidone and N,N'-dimethylimidazolidinone; and the like.

Examples of the ether solvent include:

dialiphatic ethers such as diethyl ether and dipropyl ether;

aromatic-aliphatic ethers such as anisole and phenyl ethyl ether;

diaromatic ethers such as diphenyl ether;

cyclic ethers such as tetrahydrofuran, tetrahydropyran and dioxane; and the like.

Examples of the ester solvent include;

monocarboxylic acid esters such as methyl acetate, ethyl acetate, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, ethyl propionate, n-butyl propionate, iso-amyl propionate, methyl acetoacetate and ethyl acetoacetate;

dicarboxylic acid esters such as diethyl oxalate, di-n-butyl oxalate, diethyl malonate, dimethyl phthalate and diethyl phthalate;

carboxylic acid esters of an alkylene glycol monoalkyl ether such as ethylene glycol monomethyl ether acetate, ethylene glycol monoethyl ether acetate, ethylene glycol monopropyl ether acetate, propylene glycol monomethyl ether acetate, propylene glycol monoethyl ether acetate, propylene glycol monopropyl ether acetate, propylene glycol monobutyl ether acetate and propylene glycol monomethyl ether propionate;

carboxylic acid esters of an ether group-containing alkylene glycol monoalkyl ether such as diethylene glycol monomethyl ether acetate, diethylene glycol monoethyl ether acetate, diethylene glycol mono-n-butyl ether acetate, dipropylene glycol monomethyl ether acetate, dipropylene glycol monoethyl ether acetate and diethylene glycol monomethyl ether propionate;

hydroxy acid esters such as methyl glycolate, ethyl glycolate, methyl lactate, ethyl lactate, n-butyl lactate and n-amyl lactate;

lactones such as γ-butyrolactone and γ-valerolactone;

carbonates such as diethyl carbonate and propylene carbonate; and the like.

Of these, an alcohol solvent and an ester solvent are preferred as the solvent (B).

As the alcohol solvent, monovalent aliphatic alcohols and alkylene glycol monoalkyl ethers are preferred, monovalent aliphatic alcohols having 4 or more carbon atoms, alkylene glycol monoalkyl ethers having 4 or more carbon atoms are more preferred, and butanol, isoamyl alcohol, propylene glycol monomethyl ether, propylene glycol monoethyl ether and propylene glycol monopropyl ether are still more preferred. As the ester solvent, hydroxy acid esters, lactones, carboxylic acid esters of an alkylene glycol monoalkyl ether, and carboxylic acid esters of an ether group-containing alkylene glycol monoalkyl ether are preferred, hydroxy acid esters having 4 or more carbon atoms, lactones having 4 or more carbon atoms, and monocarboxylic acid esters of an alkylene glycol monoalkyl ether having 6 or more carbon atoms are more preferred, and ethyl lactate, γ-butyrolactone and propylene glycol monomethyl ether acetate are still more preferred.

It is preferred that the solvent (B) contains substantially no water. When the solvent (B) contains substantially no water, substitution of the bridging ligand (a) with the "—O—" bridging ligand upon a reaction of the complex (A) with water can be inhibited, and consequently, deterioration of the removability by a cleaning solvent of the inorganic film-forming composition can be inhibited.

The content of the solvent (B) is such a content that gives the content of the complex (A) in the inorganic film-forming composition of preferably 0.5% by mass to 50% by mass, more preferably 2% by mass to 30% by mass, and still more preferably 5% by mass to 25% by mass.

(C) Crosslinking Accelerator

The inorganic film-forming composition may further contain (C) a crosslinking accelerator. The crosslinking accelerator (C) is a compound that generates an acid or a base by means of light or heat, and when the inorganic film-forming composition further contains the crosslinking accelerator (C), the resist pattern formability and the etching selectivity thereof can be improved. The crosslinking accelerator (C) is exemplified by an onium salt compound, an N-sulfonyloxyimide compound, and the like. The crosslinking accelerator (C) is preferably a thermal crosslinking accelerator that thermally generates an acid or a base, and among those exemplified, an onium salt compound is preferred.

The onium salt compound is exemplified by a sulfonium salt, a tetrahydrothiophenium salt, an iodonium salt, an ammonium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, triphenylsulfonium1,1,2,2-tetrafluoro-6-(1-adamantanecarbonyloxy)-hexane-1-sulfonate. and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl) tetrahydrothiophenium 2-bicyclo[2.2.1]hept-2-yl-1,1,2,2-tetrafluoroethanesulfonate, 1-(6-n-butoxynaphthalen-2-yl) tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl) tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1, 1,2,2-tetrafluoroethanesulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2, 2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and the like.

Examples of the ammonium salt include ammonium formate, ammonium maleate, ammonium fumarate, ammonium phthalate, ammonium malonate, ammonium succinate, ammonium tartrate, ammonium malate, ammonium lactate, ammonium citrate, ammonium acetate, ammonium propionate, ammonium butanoate, ammonium pentanoate, ammonium hexanoate, ammonium heptanoate, ammonium octanoate, ammonium nonanoate, ammonium decanoate, ammonium oxalate, ammonium adipate, ammonium sebacate, ammonium butyrate, ammonium oleate, ammonium stearate, ammonium linoleate, ammonium linolenate, ammonium salicylate, ammonium benzenesulfonate, ammonium benzoate, ammonium p-aminobenzoate, ammonium p-toluenesulfonate, ammonium methanesulfonate, ammonium trifluoromethanesulfonate, ammonium trifluoroethanesulfonate, and the like. In addition, ammonium salts which are derived by replacing the ammonium ion of the above-exemplified ammonium salts with a methylammonium ion, a dimethylammonium ion, a trimethylammonium ion, a tetramethylammonium ion, an ethylammonium ion, a diethylammonium ion, a triethylammonium ion, a tetraethylammonium ion, a propylammonium ion, a dipropylammonium ion, a tripropylammonium ion, a tetrapropylammonium ion, a butylammonium ion, a dibutylammonium ion, a tributylammonium ion, a tetrabutylammonium ion, a trimethylethylammonium ion, a dimethyldiethylammonium ion, a dimethylethylpropylammonium ion, a methylethylpropylbutylammonium ion, an ethanolammonium ion, a diethanolammonium ion, a triethanolammonium ion or the like are also exemplified. Furthermore, 1,8-diazabicyclo[5.4.0]undec-7-ene salts such as 1,8-diazabicyclo[5.4.0]undec-7-ene formic acid salt and 1,8-diazabicyclo[5.4.0]undec-7-ene p-toluenesulfonic acid salt, 1,5-diazabicyclo[4.3.0]-5-nonene salts such as 1,5-diazabicyclo[4.3.0]-5-nonene formic acid salt and 1,5-diazabicyclo[4.3.0]-5-nonene p-toluenesulfonic acid salt, and the like are also exemplified.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, and the like.

Of these crosslinking accelerators (C), onium salt compounds are preferred, a tetrahydrothiophenium salt, an iodonium salt and an ammonium salt are more preferred, and 1-(4-n-butoxynaphthalen-1-yl)tetrahydrothiophenium trifluoromethanesulfonate, diphenyliodonium trifluoromethanesulfonate, tetramethylammonium acetate, and 1,8-diazabicyclo[5.4.0]undec-7-ene p-toluenesulfonic acid salt are still more preferred.

These crosslinking accelerators (C) may be used either alone, or two or more types thereof may be used in combination. The content of the crosslinking accelerator (C) is preferably no less than 0 parts by mass and no greater than 10 parts by mass, and more preferably no less than 0.1 parts by mass and no greater than 5 parts by mass with respect to 100 parts by mass of the complex (A). When the content of the crosslinking accelerator (C) falls within the above range, the resist pattern formability and the etching selectivity of the inorganic film-forming composition can be further improved.

Other Optional Component

The inorganic film-forming composition may contain other optional component such as a surfactant within a range not leading to impairment of the effects of the present invention.

Surfactant

The surfactant exhibits the effect of improving coating property, striation and the like. Examples of the surfactant include: nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate; commercially available products such as KP341 (available from Shin-Etsu Chemical Co., Ltd.), Polyflow No. 75 and Polyflow No. 95 (all available from Kyoeisha Chemical Co., Ltd.), EFTOP EF301, EFTOP EF303 and EFTOP EF352 (all available from Tochem Products Co. Ltd.), Megaface F171 and Megaface F173 (all available from Dainippon Ink and Chemicals, Incorporated), Fluorad FC430 and Fluorad FC431 (all available from Sumitomo 3M Limited), ASAHI GUARD AG710, Surflon S-382, Surflon SC-101, Surflon SC-102, Surflon SC-103, Surflon SC-104, Surflon SC-105 and Surflon SC-106 (all available from Asahi Glass Co., Ltd.); and the like.

The surfactant may be used either alone, or two or more types thereof may be used in combination. Moreover, the amount of the surfactant blended may be appropriately selected in accordance with the purpose of the blending.

Preparation Method of Inorganic Film-Forming Composition for Multilayer Resist Processes The inorganic film-forming composition may be prepared, for example, by mixing the complex (A) and the solvent (B), as well as the crosslinking accelerator (C) and the other optional component(s) and the like, as needed, at a certain ratio. In use, the inorganic film-forming composition is typically prepared by dissolving the components in a solvent, followed by filtration through a filter having a pore size of, for example, about 0.2 µm.

Pattern-Forming Method

A pattern-forming method according to another embodiment of the present invention includes:

providing an inorganic film directly or indirectly on a substrate using the inorganic film-forming composition for multilayer resist processes according to the embodiment of the present invention (hereinafter, may be also referred to as "inorganic film-providing step");

forming a resist pattern directly or indirectly on the inorganic film (hereinafter, may be also referred to as "resist pattern-forming step"); and forming a pattern on the substrate by at least one dry-etching operations using the resist pattern as a mask (hereinafter, may be also referred to as "substrate pattern-forming step").

According to the pattern-forming method, since the inorganic film-forming composition described above is used, an inorganic film having a small extinction coefficient and exhibiting superior resist pattern formability and etching selectivity can be formed while superior removability by a cleaning solvent is exhibited. In addition, even when the resist film is thin, dissipation, deformation, bending and the like of the resist pattern can be inhibited, leading to a precise pattern transfer. Therefore, the pattern-forming method can also be suitably applied to pattern formation in which a further reduction in processing size is demanded.

Moreover, it is also preferred that the pattern-forming method further includes:

providing a resist underlayer film on the substrate (hereinafter, may be also referred to as "resist underlayer film-providing step"), wherein in the inorganic film-providing step, the inorganic film is provided on the resist underlayer film.

Since the inorganic film-forming composition exhibits superior etching selectivity with respect to organic materials, the resist pattern can be transferred by sequentially dry-etching the inorganic film, and the resist underlayer film which is an organic film. Hereinafter, each step will be explained.

Inorganic Film-Providing Step

In this step, an inorganic film is provided directly or indirectly on a substrate using the inorganic film-forming composition. Examples of the substrate include insulating films such as silicon oxide, silicon nitride, silicon nitride oxide and polysiloxane, as well as interlayer insulating films such as wafers covered with a low-dielectric insulating film such as Black Diamond™ (available from AMAT), SiLK™ (available from Dow Chemical) or LKD5109 (available from JSR Corporation), which are commercially available products, and the like. Moreover, a substrate patterned so as to have wiring grooves (trench), plug grooves (vias) or the like may be used as the substrate. The inorganic film may be provided by applying the inorganic film-forming composition to the top face of the substrate to provide a coating film, subjecting the coating film to a heat treatment, or a combination of irradiation with ultraviolet light and a heat treatment to allow curing thereof. The procedure for applying the inorganic film-forming composition is exemplified by a spin coating procedure, a roll coating procedure, a dip coating procedure, and the like. Moreover, the temperature of the heat treatment is typically 150° C. to 500° C., and preferably 180° C. to 350° C. The time period of the heat treatment is typically 30 sec to 1,200 sec, and preferably 45 sec to 600 sec. The condition of the irradiation with ultraviolet light may be appropriately selected in accordance with the formulation of the inorganic film-forming composition, and the like. The film thickness of the inorganic film provided is typically about 5 nm to about 50 nm.

Resist Underlayer Film-Providing Step

Alternatively, the step of providing a resist underlayer film which is an organic film on the substrate using a resist underlayer film-forming composition may be included before the inorganic film-providing step. Conventionally well-known resist underlayer film-forming compositions may be used as the aforementioned resist underlayer film-forming composition, and examples thereof include NFC HM8005 (available from JSR Corporation), and the like. The resist underlayer film may be provided by applying the resist underlayer film-forming composition on the substrate to provide a coating film, and subjecting the coating film to a heat treatment, or a combination of irradiation with ultraviolet light and a heat treatment to allow curing thereof. The procedure for applying the resist underlayer film-forming composition is exemplified by a spin coating procedure, a roll coating procedure, a dip coating procedure, and the like. Moreover, the temperature of the heat treatment is typically 150° C. to 500° C., and preferably 180° C. to 350° C. The time period of the heat treatment is typically 30 sec to 1,200 sec, and preferably 45 sec to 600 sec. The condition of the irradiation with ultraviolet light may be appropriately selected in accordance with the formulation of the resist underlayer film-forming composition. The film thickness of the resist underlayer film provided is typically about 50 nm to about 500 nm.

In addition, other underlayer film distinct from the resist underlayer film described above may be provided on the top face of the substrate. This other underlayer film is a film to which a reflection-preventing function, coating film flatness, superior etching resistance against fluorine-based gases such as $CF_4$ and/or the like are/is imparted. Commercially available products such as e.g., NFC HM8005 (available from JSR Corporation) may be used as the other underlayer film.

Resist Pattern-Forming Step

In this step, a resist pattern is formed directly or indirectly on the provided inorganic film. The procedure for forming the resist pattern is exemplified by (A) a procedure involving use of a resist composition, (B) a procedure involving nanoimprint lithography, and the like. Hereinafter, each procedure will be explained.

(A) Procedure Involving Use of Resist Composition

In a case where this procedure is employed, the resist pattern-forming step includes:

providing a resist film directly or indirectly on the inorganic film using the resist composition (hereinafter, may be also referred to as "resist film-providing step");

exposing the resist film (hereinafter, may be also referred to as "exposure step"); and developing the exposed resist film (hereinafter, may be also referred to as "development step").

Each step will be explained below.

Resist Film-Providing Step

In this step, a resist film is provided directly or indirectly on the inorganic film using the resist composition. The resist composition is exemplified by: a resist composition that contains a polymer including an acid-labile group, and a radiation-sensitive acid generating agent; a positive type resist composition that contains an alkali-soluble resin and a quinone diazide photosensitizing agent; a negative type resist composition that contains an alkali-soluble resin and a crosslinking agent; and the like. Commercially available resist compositions may be used as the resist composition. The resist composition may be applied by, for example, a conventional procedure such as a spin coating procedure. It is to be noted that in applying the resist composition, the amount of the resist composition applied is adjusted such that the resulting resist film has a desired film thickness.

The resist film can be formed by subjecting the coating film formed through the application of the resist composition to prebaking (PB) or the like, and thereby evaporating the solvent in the coating film. The temperature of the PB may be appropriately adjusted in accordance with the type of the resist composition employed, and the like; the temperature of the PB is preferably 30° C. to 200° C., and more preferably 50° C. to 150° C. The time period of the PB is typically 30 sec to 200 sec, and preferably 45 sec to 120 sec. The film thickness of the resist film formed is typically 1 nm to 500 nm, and preferably 10 nm to 300 nm. It is to be noted that other film may be further provided on the surface of the resist film.

Exposure Step

In this step, the provided resist film is exposed. This exposure is typically executed by selectively irradiating the resist film with a radioactive ray through a photomask. The radioactive ray employed in the exposure may be appropriately selected in accordance with the type of the acid generating agent contained in the resist composition, from e.g., electromagnetic waves such as visible light rays, ultraviolet rays, far ultraviolet rays, X-rays and γ-rays; particle rays such as electron beams, molecular beams and ion beams; and the like. However, far ultraviolet rays are preferred, and a KrF excimer laser beam (248 nm), an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm), and extreme-ultraviolet rays (wavelength: 13 nm, etc.) are more preferred. The exposure may also be executed through a liquid immersion medium. In such an exposure, a liquid immersion upper layer film may be provided on the resist film using a liquid immersion upper layer film-forming composition.

In order to improve the resolution, the pattern profile, the developability, etc. of the resist film, post-baking is preferably executed after the exposure. The temperature of the post-baking may be appropriately adjusted in accordance with the type of the resist composition employed and the like; the temperature of the post-baking is preferably 50° C. to 180° C., and more preferably 70° C. to 150° C. The time period of the post-baking is typically 30 sec to 200 sec, and preferably 45 sec to 120 sec.

Development Step

In this step, the exposed resist film is developed. The developer solution which may be used in the development may be appropriately selected in accordance with the type of the resist composition employed. In the case of: the resist composition that contains a polymer including an acid-labile group, and a radiation-sensitive acid generating agent; or the positive type resist composition that contains an alkali-soluble resin, an aqueous alkaline solution of, e.g., sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide (TMAH), tetraethylammonium hydroxide, pyrrole, piperidine, choline, 1,8-diazabicyclo[5.4.0]-7-undecene, 1,5-diazabicyclo[4.3.0]-5-nonene or the like may be employed, and thereby a positive type resist pattern can be formed. Of these, an aqueous TMAH solution is preferred. An appropriate amount of a water soluble organic solvent, e.g., an alcohol such as methanol and ethanol and/or a surfactant may be added to these aqueous alkaline solutions. Moreover, in the case of the resist composition that contains a polymer including an acid-labile group, and a radiation-sensitive acid generating agent, a liquid containing an organic solvent may be used as the developer solution, and thereby a negative type resist pattern can be formed. Thus, by using the resist composition that contains a polymer including an acid-labile group, and a developer solution containing an organic solvent, a finer resist pattern can be formed, and, in turn, a finer substrate pattern can be formed. Examples of the organic solvent include solvents similar to those exemplified in connection with the solvent (B) of the inorganic film-forming composition, and the like. Of these, ester solvents are preferred, and butyl acetate is more preferred.

Alternatively, in the case of the negative type chemical amplification resist composition, or the negative type resist that contains an alkali-soluble resin, an aqueous solution of an alkali, e.g.: an inorganic alkalis such as sodium hydroxide, potassium hydroxide, sodium carbonate, sodium silicate, sodium metasilicate or aqueous ammonia; a primary amine such as ethylamine or n-propylamine; a secondary amine such as diethylamine or di-n-butylamine; a tertiary amine such as triethylamine or methyldiethylamine; an alcoholamine such as dimethylethanolamine or triethanolamine; a quaternary ammonium salt such as tetramethylammonium hydroxide, tetraethylammonium hydroxide or choline; a cyclic amine such as pyrrole or piperidine, or the like may be employed.

(B) Procedure Involving Nanoimprint Lithography

In a case where this procedure is employed, the resist pattern-forming step includes:

forming a resist pattern on the inorganic film by nanoimprint lithography using a resist composition (hereinafter, may be also referred to as "resist pattern-forming step by nanoimprint lithography").

This step will be explained below.

Resist Pattern-Forming Step by Nanoimprint Lithography

In this step, a resist pattern is formed on the inorganic film by nanoimprint lithography using a resist composition. More specifically describing this step, this process includes: providing a pattern formation layer on the inorganic film (hereinafter, may be also referred to as "pattern formation layer-providing step"); subjecting the surface of a mold having a reversal pattern on the surface thereof to a hydrophobilization treatment (hereinafter, may be also referred to as "hydrophobilization treatment step"); pressing the hydrophobized surface of the mold on the pattern formation layer (hereinafter, may be also referred to as "pressing step"); exposing the pattern formation layer while the mold is pressed (hereinafter, may be also referred to as "exposure step"); and releasing the mold from the exposed pattern formation layer (hereinafter, may be also referred to as "releasing step").

Hereinafter, each step will be explained.

Pattern Formation Layer-Providing Step

In this step, a pattern formation layer is provided on the inorganic film. A material constituting the pattern formation layer is a radiation-sensitive composition for nanoimprinting. The pattern formation layer may contain, in addition to the radiation-sensitive composition for nanoimprinting, a curing accelerator, and the like. The curing accelerator is exemplified by a radiation-sensitive curing accelerator and thermal curing accelerator. Of these, the radiation-sensitive curing accelerator is preferred. The radiation-sensitive curing accelerator may be appropriately selected in accordance with constituent units constituting the radiation-sensitive composition for nanoimprinting, and examples thereof include photoacid generating agents, photobase generating agents and photosensitizing agents, and the like. It is to be noted that the radiation-sensitive curing accelerator may be used either alone, or two or more types thereof may be used in combination.

Examples of the procedure for applying the radiation-sensitive composition include an ink jet procedure, a dip coating procedure, an air knife coating procedure, a curtain coating procedure, a wire bar coating procedure, a gravure coating procedure, an extrusion coating procedure, a spin coating procedure, slit scan procedure, and the like.

Hydrophobilization Treatment Step

In this step, the surface of a mold having a reversal pattern on the surface thereof is subjected to a hydrophobilization treatment. The mold needs to be made from an optically transparent material. Examples of the optically transparent material include: glass; quartz; optically transparent resins such as PMMA and polycarbonate resin; transparent metal vapor deposition films; flexible films such as polydimethylsiloxane; photo-curable films; metal films; and the like.

For example, a release agent or the like is used in the hydrophobilization treatment. Examples of the release agent include silicon-containing release agents, fluorine-containing release agents, polyethylene-containing release agents, polypropylene-containing release agents, paraffin-containing release agents, montan-containing release agents, carnauba-containing release agents, and the like. It is to be noted that the release agent may be used either alone, or two or more types thereof may be used in combination. Of these, silicon-containing release agents are preferred. Examples of the silicon-containing release agent include polydimethylsiloxanes, acryl silicone graft polymers, acrylsiloxanes, arylsiloxanes, and the like.

Pressing Step

In this step, the hydrophobized surface of the mold is pressed on the pattern formation layer. By pressing the mold having a relief pattern on the pattern formation layer, the relief pattern of the mold is transferred to the pattern formation layer. The pressure in pressing the mold is typically 0.1 MPa to 100 MPa, preferably 0.1 MPa to 50 MPa, and more preferably 0.1 MPa to 30 MPa. The time period of the pressing is typically 1 sec to 600 sec, preferably 1 sec to 300 sec, and more preferably 1 sec to 180 sec.

Exposure Step

In this step, the pattern formation layer is exposed while the mold is pressed. Upon the exposure of the pattern formation layer, a radical species is generated from a photopolymerization initiator contained in the radiation-sensitive composition for nanoimprinting. Thus, the pattern formation layer constituted with the radiation-sensitive composition for nanoimprinting is cured while the relief the pattern of mold is transferred thereto. Due to the transfer of the relief pattern, the resulting film can be used as: a film for interlayer insulating films in semiconductor elements such as, for example, LSI, system LSI, DRAM, SDRAM, RDRAM and D-RDRAM; a resist film for use in the production of semiconductor elements; and the like.

Alternatively, in a case where the pattern formation layer has a thermosetting property, heat curing may be further executed. When the heat curing is executed, the heating atmosphere, the heating temperature and the like are not particularly limited; for example, heating may be executed at 40° C. to 200° C. under an inert atmosphere or under a reduced pressure. The heating can be carried out using a hot plate, an oven, a furnace, or the like.

Releasing Step

In this step, the mold is released from the exposed pattern formation layer. The releasing procedure is not particularly limited; for example, releasing may be achieved by moving the mold away from a base with the base fixed, or releasing may be achieved by moving the base away from the mold with the mold fixed. Alternatively, releasing may be achieved by pulling the base and the mold toward the opposite direction.

Substrate Pattern-Forming Step

In this step, a pattern is formed on the substrate by at least one dry-etching operations using the resist pattern as a mask. It is to be noted that in a case where the resist underlayer film is provided, the inorganic film, the resist underlayer film and the substrate are sequentially dry-etched using the resist pattern as a mask, whereby the pattern is formed. The dry-etching may be executed using a well-known dry-etching apparatus. In addition, examples of the gas which may be used as a source gas in the dry-etching include: oxygen atom-containing gases such as $O_2$, CO and $CO_2$; inert gases such as He, $N_2$ and Ar; chlorine-containing gases such as $Cl_2$ and $BCl_3$; fluorine-containing gases such as $CHF_3$ and $CF_4$; other gases such as $H_2$ and $NH_3$, which may be selected depending on the elemental composition of the substance to be etched. It is to be noted that these gases may also be used in mixture.

EXAMPLES

Hereinafter, the embodiments of the present invention will be explained in more detail by way of Examples, but the present invention is not in any way limited to these Examples. Measuring methods for physical properties in Examples are shown below.

Number Average Molecular Weight (Mn)

The Mn of the complex (A) was determined by gel permeation chromatography using a GPC column (SHODEX A-80M, length: 50 cm, available from Showa Denko K.K.) under the condition involving the following:

apparatus: high temperature high performance gel permeation chromatograph (model: 1500-C, ALC/GPC, available from Waters Corporation);

column temperature: 40° C.;

elution solvent: tetrahydrofuran (available from Wako Pure Chemical Industries, Ltd.);

flow rate: 1.0 mL/min;

sample concentration: 0.1 g/10 mL;

detector: differential refractometer; and standard substance: standard polystyrene (available from Pressure Chemical Company).

Solid Content Concentration

On an aluminum dish which had been weighed to confirm the mass of (A (g)) was placed 1.00 g of a solution as a test sample for the solid content concentration, and the aluminum dish was heated on a hot plate at 200° C. for 1 hour in an ambient air. Thereafter the aluminum dish was cooled to room temperature, and then the mass (B(g)) of the aluminum dish (including the residues) was measured. A value of (B−A)*100(%) was calculated using the values of the mass, A and B, to determine the solid content concentration of the solution.

Synthesis of Complex (A)

Compounds used in the synthesis of the complex (A) are shown below.

M-1: yttrium(III) isopropoxide

M-2: titanium(IV) isopropoxide

M-3: titanium(IV) butoxide oligomeric tetramer ([TiO$(OBu)_2]_4$)

M-4: zirconium(IV) butoxide

M-5: hafnium(IV) ethoxide

M-6: tantalum(V) ethoxide

M-7: tungsten(VI) methoxide

M-8: tetrakis(t-butoxy)(oxo)tungsten(VI) (WO(OBu-t)$_4$)

M-9: aluminum(III) chloride

M-10: methyltrimethoxysilane

M-11: titanium(IV) butoxide oligomeric decamer ([TiO$(OBu)_2]_{10}$)

M-12: zirconium di-n-butoxide bis(2,4-pentanedionate) (60% by mass concentration; butanol solution)

M-13: titanium diisopropoxide bis(ethyl acetoacetate)

M-14: tetramethyl orthosilicate

Synthesis Example 1

After 26.6 g of the compound (M-1) and 100 g of tetrahydrofuran (THF) were mixed and stirred at 25° C. for 10 min, 20.7 g of 1,4-benzenedimethanol was added. The temperature of the mixture was elevated to 60° C., and the mixture was stirred with heating for 4 hrs. After the completion of the reaction, the mixture was cooled to room temperature, 10.0 g of acetylacetone (AcAc) and 200 g of propylene glycol monomethyl ether (PGME) were added thereto, and then matter having a low boiling point was removed using an evaporator, whereby a solution of a complex (A-1) with a solid content concentration of 10.0% by mass was obtained. The Mn of the complex (A-1) was 3,500.

Synthesis Example 2

After 28.4 g of the compound (M-2) and 100 g of tetrahydrofuran (THF) were mixed and stirred at 25° C. for 10 min, 15.2 g of propylene glycol was mixed therewith. The temperature of the mixture was elevated to 60° C., and the mixture was stirred with heating for 4 hrs. After the completion of the reaction, the mixture was cooled to room temperature, 13.1 g of ethyl acetoacetate (EAcAc) and 200 g of propylene glycol monoethyl ether (PGEE) were added thereto, and then matter having a low boiling point was removed using an evaporator, whereby a solution of a complex (A-2) with a solid content concentration of 10.0% by mass was obtained. The Mn of the complex (A-2) was 4,600.

Synthesis Example 3

After 9.7 g of the compound (M-3) and 50 g of butanol (BuOH) were mix and stirred at 25° C. for 10 min, 17.4 g of maleic acid was mixed therewith, and the mixture was stirred with heating at 25° C. for 4 hrs. After the addition of 200 g of ethyl lactate (EL), matter having a low boiling point was removed using an evaporator, whereby a solution of a complex (A-3) with a solid content concentration of 10.0% by mass was obtained. The Mn of the complex (A-3) was 2,300.

Comparative Synthesis Example 1

A solution of a complex (a-3) with a solid content concentration of 10% by mass was obtained by a similar operation to that of Synthesis Example 3 except that maleic acid was not used. The Mn of the complex (a-3) was 1,100.

Synthesis Example 4

After 38.3 g of the compound (M-4) and 50 g of propylene glycol monomethyl ether (PGME) were mixed and stirred at 25° C. for 10 min, 9.2 g of glycerin was mixed therewith. The mixture was stirred with heating at 100° C. for 4 hrs. After the completion of the reaction, the mixture was cooled to room temperature, 20.2 g of diethyl 1,3-acetonedicarboxylate (ADC) and 200 g of γ-butyrolactone (GBL) were added thereto, and then matter having a low boiling point was removed using an evaporator, whereby a solution of a complex (A-4) with a solid content concentration of 10.0% by mass was obtained. The Mn of the complex (A-4) was 7,900.

Synthesis Example 5

After 35.9 g of the compound (M-5) and 1,000 g of tetrahydrofuran (THF) were mixed and stirred at 25° C. for 10 min, 33.4 g of hexamethylene diisocyanate was mixed therewith. The mixture was stirred with heating at 40° C. for 4 hrs. After the completion of the reaction, the mixture was cooled to room temperature, 5.0 g of acetylacetone (AcAc) and 200 g of propylene glycol monoethyl ether (PGEE) were added, and then matter having a low boiling point was removed using an evaporator, whereby a solution of a complex (A-5) with a solid content concentration of 10.0% by mass was obtained. The Mn of the complex (A-5) was 6,100.

Synthesis Example 6

After 10.0 g of the compound (M-6) and 100 g of tetrahydrofuran (THF) were mixed and stirred at 25° C. for 10 min, 6.5 g of diethylene glycol was mixed therewith. The mixture was stirred with heating at 60° C. for 4 hrs. After the completion of the reaction, the mixture was cooled to room temperature, the solvent was once removed completely using an evaporator, and nonvolatile components were dried. Thereafter, ethyl lactate (EL) was added, whereby a solution of a complex (A-6) with a solid content concentration of 10.0% by mass was obtained. The Mn of the complex (A-6) was 2,900.

Comparative Synthesis Example 2

A solution of a complex (a-2) with a solid content concentration of 10% by mass was obtained by a similar operation to that of Synthesis Example 6 except that diethylene glycol was not used. The Mn of the complex (a-2) was 450.

Synthesis Example 7

After 3.7 g of the compound (M-7) and 75 g of butanol (BuOH) were mixed and stirred at 25° C. for 10 min, 3.5 g of succinic acid was mixed therewith. The mixture was stirred with heating at 100° C. for 12 hrs. After the completion of the reaction, the mixture was cooled to room temperature, 0.6 g of ethyl acetoacetate (EAcAc) was added. The mixture was stirred for 10 min, and then matter having a low boiling point was removed using an evaporator, whereby a solution of a complex (A-7) with a solid content concentration of 10.0% by mass (S-7) was obtained. The Mn of the complex (A-7) was 8,000.

Synthesis Example 8

After 3.0 g of the compound (M-8) and 27 g of tetrahydrofuran (THF) were mixed, 0.6 g of acetylacetone (AcAc) was added thereto, and then the mixture was stirred at 25° C. for 10 min. After addition of 60 g of butanol (BuOH), the mixture was further stirred at 25° C. for 10 min. Next, 1.0 g of diethylene glycol was added, and the mixture was stirred at 25° C. for 5 hrs. After the completion of the reaction, matter having a low boiling point was removed using an evaporator, whereby a solution of a complex (A-8) with a solid content concentration of 10.0% by mass was obtained. The Mn of the complex (A-8) was 1,200.

Comparative Synthesis Example 3

A solution of a complex (a-3) with a solid content concentration of 10% by mass was obtained by a similar operation to that of Synthesis Example 8 except that acetylacetone was not used. The Mn of the complex (a-3) was 900.

Synthesis Example 9

After 1.3 g of the compound (M-9) and 50 g of toluene were mixed, 0.9 g of N,N'-dimethylethylenediamine was added thereto. The mixture was stirred at 25° C. for 10 min, and then at 60° C. for 5 hrs. After the completion of the reaction, 0.6 g of ethyl acetoacetate (EAcAc) and 200 g of propylene glycol monomethyl ether acetate (PGMEA) were added, and then matter having a low boiling point was removed using an evaporator, whereby a solution of a complex (A-9) with a solid content concentration of 10.0% by mass was obtained. The Mn of the complex (A-9) was 4,700.

Comparative Synthesis Example 4

After 13.6 g of the compound (M-10) and 100 g of tetrahydrofuran (THF) were mixed and stirred at 25° C. for 10 min, 15.9 g of diethylene glycol was mixed therewith. The temperature of the mixture was elevated to 60° C., and the mixture was stirred with heating for 4 hrs. After the completion of the reaction, the mixture was cooled to room temperature, 10.0 g of acetylacetone (AcAc) and 200 g of propylene glycol monomethyl ether (PGME) were added thereto, and then matter having a low boiling point was removed using an evaporator, whereby a solution of a complex (a-4) with a solid content concentration of 10.0% by mass was obtained. The Mn of the complex (a-4) was 2,500.

Comparative Synthesis Example 5

The compound (M-11) in an amount of 15.0 g was dissolved in 15.0 g of propylene glycol monomethyl ether (PGME). To this solution was added a solution prepared by dissolving 19.52 g of ethyl acetoacetate (EAcAc) in 15.0 g of PGME, and the mixture was stirred at room temperature for 4 hrs. Next, 1.5 g of trimethylolpropane ethoxylate was added to this mixture, and then the mixture was stirred for 1 hour. Thereafter, PGME was added, whereby a solution of a complex (a-5) with a solid content concentration of 10.0% by mass was obtained. The Mn of the complex (a-5) was 5,100.

Comparative Synthesis Example 6

The compound (M-12) in an amount of 16.67 g was dissolved in 99.59 g of propylene glycol monopropyl ether (PGPE). To this solution was added 0.41 g of water, and then the mixture was stirred at room temperature for 24 hrs. Next, to this reaction liquid, 2.5 g of 2-cyano-3-(4-hydroxyphenyl)-acrylic acid ethyl ether (CHAE) was added, and the mixture was stirred for 1 hour. Thereafter, PGPE was added, whereby a solution of a complex (a-6) with a solid content concentration of 10.0% by mass was obtained. The Mn of the complex (a-6) was 3,100.

Comparative Synthesis Example 7

The compound (M-13) in an amount of 10.00 g and the compound (M-14) in an amount of 1.23 g were dissolved in 112.30 g of propylene glycol monopropyl ether (PGPE). Then, to this solution was added 0.64 g of water, and the mixture was stirred at room temperature for 24 hrs. Next, to this reaction liquid, 6.2 g of vanillin was added, and the mixture was stirred for 1 hour to prepare an antireflection preparation. Then, PGPE was added, whereby a solution of a complex (a-7) with a solid content concentration of 10.0% by mass was obtained. The Mn of the complex (a-7) was 4,500.

The metal compound, the compound giving the bridging ligand (a), and the compound giving the ligand (b) which were used in the aforementioned Synthesis Examples and Comparative Synthesis Examples, as well as the solvent (B) used in the preparation of the inorganic film-forming compositions are shown in Table 1 below. It is to be noted that "solvent" set forth in the column in Table 1 showing the "amount" of the compound giving the ligand (b) indicates that the compound giving the ligand (b) was also used as the solvent (B).

TABLE 1

| | (A) Complex | Metal compound type | amount (mol) | Compound giving bridging ligand (a) type | amount (mol) | Compound giving ligand (b) compound | amount (mol) | (B) Solvent | Mn |
|---|---|---|---|---|---|---|---|---|---|
| Synthesis Example 1 | A-1 | M-1 | 0.10 | 1,4-benzenedimethanol | 0.15 | AcAc | 0.10 | PGME | 3,500 |
| Synthesis Example 2 | A-2 | M-2 | 0.10 | propylene glycol | 0.20 | EAcAc | 0.10 | PGEE | 4,600 |
| Synthesis Example 3 | A-3 | M-3 | 0.010 | maleic acid | 0.15 | EL | solvent | EL | 2,300 |
| Synthesis Example 4 | A-4 | M-4 | 0.10 | glycerin | 0.10 | ADC | 0.14 | GBL | 7,900 |
| Synthesis Example 5 | A-5 | M-5 | 0.10 | hexamethylene diisocyanate | 0.20 | AcAc | 0.050 | PGEE | 6,100 |
| Synthesis Example 6 | A-6 | M-6 | 0.025 | diethylene glycol | 0.061 | EL | solvent | EL | 2,900 |
| Synthesis Example 7 | A-7 | M-7 | 0.010 | succinic acid | 0.030 | EAcAc | 0.005 | BuOH | 8,000 |
| Synthesis Example 8 | A-8 | M-8 | 0.006 | diethylene glycol | 0.009 | AcAc | 0.006 | BuOH | 1,200 |
| Synthesis Example 9 | A-9 | M-9 | 0.010 | N,N'-dimethylethylenediamine | 0.010 | EAcAc | 0.005 | PGMEA | 4,700 |
| Comparative Synthesis Example 1 | a-1 | M-3 | 0.010 | — | — | EL | solvent | EL | 1,100 |
| Comparative Synthesis Example 2 | a-2 | M-6 | 0.025 | — | — | EL | solvent | EL | 450 |
| Comparative Synthesis Example 3 | a-3 | M-8 | 0.006 | diethylene glycol | 0.009 | — | — | BuOH | 900 |
| Comparative Synthesis Example 4 | a-4 | M-10 | 0.10 | diethylene glycol | 0.15 | AcAc | 0.10 | PGME | 2,500 |
| Comparative Synthesis Example 5 | a-5 | M-11 | 0.071 | trimethylol ethoxylate | 0.006 | EAcAc | 0.150 | PGME | 5,100 |
| Comparative Synthesis Example 6 | a-6 | M-12 | 0.023 | H$_2$O CHAE | 0.023 0.012 | — | — | PGPE | 3,100 |
| Comparative Synthesis Example 7 | a-7 | M-13 M-14 | 0.024 0.008 | H$_2$O vanillin | 0.036 0.041 | — | — | PGPE | 4,500 |

Preparation of Inorganic Film-Forming Composition for Multilayer Resist Processes The crosslinking accelerators (C) used in the preparation of the inorganic film-forming composition are shown below.

(C) Crosslinking Accelerator

C-1: diphenyliodonium trifluoromethanesulfonate

C-2: 1-(4-n-butoxynaphthalen-1-yl)tetrahydrothiophenium trifluoromethanesulfonate C-3: tetramethylammonium acetate C-4: 1,8-diazabicyclo[5.4.0]undec-7-ene p-toluenesulfonic acid salt Example 1

After 0.38 parts by mass of the crosslinking accelerator (C-1) was added to 100.0 parts by mass (the amount of the solid content thereof: 10.0 parts by mass) of the solution of the complex (A-1) obtained above, the resulting solution was filtered through a filter having a pore size of 0.2 μm, whereby an inorganic film-forming composition for multilayer resist processes (J-1) was prepared.

Examples 2 to 9 and Comparative Examples 1 to 7

Inorganic film-forming compositions for multilayer resist processes (J-2) to (J-9) and (CJ-1) to (CJ-7) were prepared by a similar operation to that of Example 1 except that 100.0 parts by mass (the amount of the solid content thereof: 10.0 parts by mass) of solutions of the component (A) of the type shown in Table 2 was used, and that the type and the amount of the crosslinking accelerator (C) used as needed were as shown in Table 2. It is to be noted that "—" indicates that the corresponding component was not used.

Evaluations

The prepared inorganic film-forming compositions for multilayer resist processes were evaluated according to the following methods. The results of the evaluations are shown together in Table 2.

Removability by Cleaning Solvent

Each inorganic film-forming composition was dropped on a silicon wafer as a substrate, and thereafter the substrate was rotated at 1,000 rpm for 30 sec, whereby a coating film (unheated film) was provided. A part of this coating film was immersed for 1 min in γ-butyrolactone as a cleaning solvent for cleaning the edge and the back face of the substrate, and then was dried using an air spray gun. A degree of removal of the unheated film in this process was evaluated according to the following criteria:

A: complete removal of the film being identified by visual inspection;

B: failure of removal at a part of the film being identified by visual inspection; and C: entirely undissolved film being identified by visual inspection.

Extinction Coefficient of Inorganic Film

Each inorganic film-forming composition was applied on a silicon wafer as a substrate by using a spin coater, followed by baking on a hot plate at 250° C. for 60 sec, whereby an inorganic film having a film thickness of 20 nm was provided. The extinction coefficient of the inorganic film was determined using an ellipsometer (SL-200, available from Rudolph Technologies, Inc.). Values of the extinction coefficient thus determined are shown in Table 2.

Resist Pattern Formability

Resist Composition: Development with Alkali

A resist underlayer film-forming composition (NFC HM8005, available from JSR Corporation) was applied on a silicon wafer as a substrate using a spin coater, followed by drying on a hot plate at 250° C. for 60 sec, whereby a resist underlayer film having a film thickness of 300 nm was provided. Each inorganic film-forming composition was applied on the provided resist underlayer film using a spin coater, followed by baking on a hot plate at 250° C. for 60 sec, whereby an inorganic film having a film thickness of 20 nm was provided. A resist composition (ARX2014J, available from JSR Corporation) was applied on the provided inorganic film, followed by drying at 90° C. for 60 sec, whereby a resist film having a film thickness of 100 nm was provided. A liquid immersion upper layer film-forming composition (NFC TCX091-7, available from JSR Corporation) was applied on the provided resist film, followed by drying at 90° C. for 60 sec, whereby a liquid immersion upper layer film having a film thickness of 30 nm was provided. Next, an exposure was executed by a liquid immersion exposure process at an exposure dose of 16 mJ/cm$^2$ through a photomask for forming a line-and-space pattern in which both lines and spaces had a width of 50 nm, using an ArF excimer laser irradiation apparatus (S610C, available from NIKON Corporation), and thereafter the substrate including the resist film was heated at 115° C. for 60 sec. Then, a development was executed for 30 sec using a 2.38% by mass aqueous tetramethylammonium hydroxide solution as a developer solution, whereby a 50 nm 1L/1S resist pattern was formed. The formed resist pattern was observed using a scanning electron microscope (available from Hitachi High-Technologies Corporation), and in the 50 nm line-and-space pattern, the resist pattern formability was evaluated to be: "A (favorable)" in a case where the resist pattern did not spread toward the bottom; and "B (unfavorable)" in a case where the resist pattern spread toward the bottom. A pattern transfer was carried out by sequentially dry-etching the inorganic film and the substrate using the formed resist pattern as a mask, and a dry-etching apparatus (Telius SCCM, available from Tokyo Electron Limited).

Resist Composition: Development with Organic Solvent

A resist underlayer film-forming composition (NFC HM8005, available from JSR Corporation) was applied on a silicon wafer as a substrate using a spin coater, followed by drying on a hot plate at 250° C. for 60 sec, whereby a resist underlayer film having a film thickness of 300 nm was provided. Each inorganic film-forming composition was applied on the provided resist underlayer film using a spin coater, followed by baking on a hot plate at 250° C. for 60 sec, whereby an inorganic film having a film thickness of 20 nm was provided. A resist composition (ARX2014J, available from JSR Corporation) was applied on the provided inorganic film, followed by drying at 90° C. for 60 sec, whereby a resist film having a film thickness of 100 nm was provided. A liquid immersion upper layer film-forming composition (NFC TCX091-7, available from JSR Corporation) was applied on the provided resist film, followed by drying at 90° C. for 60 sec, whereby a liquid immersion upper layer film having a film thickness of 30 nm was provided. Next, an exposure was executed by a liquid immersion exposure process at an exposure dose of 16 mJ/cm$^2$ through a photomask for forming a line-and-space pattern in which both lines and spaces had a width of 40 nm, using an ArF excimer laser irradiation apparatus (S610C, NIKON Corporation), and thereafter the substrate including the resist film was heated at 115° C. for 60 sec. Then, a puddle development was executed for 30 sec using butyl acetate as a developer solution, and thereafter rinsing was executed with methylisobutylcarbinol (MIBC). After spin-drying at 2,000 rpm for 15 sec, a 40 nm 1L/1S resist pattern was formed. The formed resist pattern was observed using a scanning electron microscope (available from Hitachi High-Technologies Corporation). In the 40 nm line-and-space pattern, the resist pattern formability was evaluated to be: "A (favorable)" in a case where the resist pattern did not spread toward the bottom; and "B (unfavorable)" in a case where the resist pattern spread toward the bottom. A pattern transfer was carried out by sequentially dry-etching the inorganic film and the substrate using the formed resist pattern as a mask, and a dry-etching apparatus (Telius SCCM, available from Tokyo Electron Limited).

Nanoimprint Lithography

A resist underlayer film-forming composition (NFC HM8005, available from JSR Corporation) was applied on a silicon wafer as a substrate using a spin coater, followed by drying on a hot plate at 250° C. for 60 sec, whereby a resist underlayer film having a film thickness of 300 nm was provided. Each inorganic film-forming composition was applied on the provided resist underlayer film using a spin coater, followed by baking on a hot plate at 250° C. for 60 sec, whereby an inorganic film having a film thickness of 20 nm was provided. About 50 μL of an UV-curable composition was spotted on the provided inorganic film in the center of the substrate, and the substrate was mounted on a work stage of a simplified imprinting apparatus (EUN-4200, available from Engineering System Co., Ltd.). Separately, a quartz template (NIM-PH350, available from NTT-ATN Corporation) to which a release agent (HD-1100Z, available from Daikin Chemicals) was applied beforehand according to a given procedure was attached to a quartz exposure head of the simplified imprinting apparatus by using silicone rubber (thickness: 0.2 mm) as an adhesion layer. Then, the pressure in the simplified imprinting apparatus was adjusted to 0.2 MPa, then the exposure head was moved downward such that the template for forming a line-and-space pattern in which both lines and spaces had a width of 50 nm were brought into close contact with the substrate via a photo-curable composition for nanoimprinting, and then an UV exposure was carried out for 15 sec. After 15 sec, the exposure head was elevated, the template was released from the cured and shape-transferred layer, whereby a pattern was formed. The formed resist pattern was observed using a scanning electron microscope (available from Hitachi High-Technologies Corporation), and in the 50 nm 1L/1S pattern, the resist pattern formability was determined as: "A (favorable)" in a case where the resist pattern was rectangular without any chipping; and "B (unfavorable)" in a case where a pattern loss was found.

Etching Selectivity

The inorganic films were etched according to the following two methods using the aforementioned etching apparatus, and etching selectivity was evaluated:

(1) under conditions in which the aforementioned resist underlayer film (NFC HM8005) was etched at a rate of 200 nm per min; and (2) under conditions in which the silicon dioxide film was etched at a rate of 100 nm per min.

Under each etching condition, the etching selectivity was evaluated to be: "S (Superior)" in a case where a difference between the initial film thickness of the inorganic film and the film thickness of the inorganic film after the etching was less than 2 nm; "A (favorable)" in a case where the difference was no less than 2 nm and less than 5 nm; and "B (unfavorable)" in a case where the difference was no less than 5 nm. In regard to the inorganic film-forming composition whose etching selectivity was evaluated to be superior or favorable, the inorganic films formed from such inorganic film-forming compositions each can favorably serve as a mask film in the processing of each film (i.e., the resist underlayer film or the silicon dioxide film).

TABLE 2

| | Inorganic film-forming composition for multilayer resist processes | (A) Complex type | (B) Solvent type | (C) Crosslinking accelerator type | (C) Crosslinking accelerator amount with respect to 100 parts by mass of complex (A) (parts by mass) | Evaluations removability by cleaning solvent | extinction coefficient | development with alkali | development with organic solvent | nanoimprint lithography | resist pattern formability resist underlayer film | etching selectivity silicon dioxide film |
|---|---|---|---|---|---|---|---|---|---|---|---|---|
| Example 1 | J-1 | A-1 | PGME | C-1 | 3.8 | A | 0.42 | A | A | A | A | A |
| Example 2 | J-2 | A-2 | PGEE | C-2 | 0.5 | A | 0.35 | A | A | A | S | S |
| Example 3 | J-3 | A-3 | EL | — | — | A | 0.32 | A | A | A | S | S |
| Example 4 | J-4 | A-4 | GBL | C-3 | 1.0 | A | 0.25 | A | A | A | S | S |
| Example 5 | J-5 | A-5 | PGEE | C-4 | 0.7 | A | 0.37 | A | A | A | S | S |
| Example 6 | J-6 | A-6 | EL | — | — | A | 0.33 | A | A | A | A | A |
| Example 7 | J-7 | A-7 | BuOH | C-1 | 4.0 | A | 0.38 | A | A | A | A | A |
| Example 8 | J-8 | A-8 | BuOH | — | — | A | 0.32 | A | A | A | A | A |
| Example 9 | J-9 | A-9 | PGMEA | C-2 | 0.5 | A | 0.15 | A | A | A | S | S |
| Comparative Example 1 | CJ-1 | a-1 | EL | — | — | A | 0.54 | A | A | A | A | A |
| Comparative Example 2 | CJ-2 | a-2 | EL | — | — | A | 0.63 | A | A | A | A | A |
| Comparative Example 3 | CJ-3 | a-3 | BuOH | — | — | C | 0.41 | A | A | A | A | A |
| Comparative Example 4 | CJ-4 | a-4 | PGME | — | — | A | 0.05 | A | A | A | B | B |
| Comparative Example 5 | CJ-5 | a-5 | PGME | — | — | B | 0.51 | A | A | A | A | A |
| Comparative Example 6 | CJ-6 | a-6 | PGPE | — | — | B | 0.45 | A | A | A | A | A |

TABLE 2-continued

| Inorganic film-forming composition for multilayer resist processes | (A) Complex type | (B) Solvent type | (C) Crosslinking accelerator | | Evaluations | | | | | | |
|---|---|---|---|---|---|---|---|---|---|---|---|
| | | | | | | | resist pattern formability | | | etching selectivity | |
| | | | type | amount with respect to 100 parts by mass of complex (A) (parts by mass) | removability by cleaning solvent | extinction coefficient | development with alkali | development with organic solvent | nanoimprint lithography | resist underlayer film | silicon dioxide film |
| Comparative Example 7 | CJ-7 | a-7 | PGPE | — | — | B | 0.38 | A | A | A | A | A |

As is clear from the results set forth in Table 2, it is seen that inorganic films formed from the inorganic film-forming compositions according to Examples exhibited, after application and spin-drying of the composition to provide the inorganic film, favorable solubility in a solvent for cleaning the edge and the back face of a substrate, and, after baking, had a small extinction coefficient, and exhibited superior etching selectivity and superior resist pattern formability of a resist pattern subsequently formed.

The embodiments of the present invention can provide: an inorganic film-forming composition for multilayer resist processes that forms an inorganic film which exhibits, after application and spin-drying of the composition to provide the inorganic film, favorable solubility in a solvent for cleaning the edge and the back face of a substrate and, after baking, has a small extinction coefficient, and that exhibits superior resist pattern formability and etching selectivity; and a pattern-forming method. Therefore, in a multilayer resist process employing the inorganic film-forming composition, an inorganic film formed after application and spin-drying of the composition exhibits a superior performance in removing the thus provided film by an organic solvent at a site on the substrate where the inorganic film should be removed, and even when a thinner organic film is to be provided, dissipation, deformation, bending and the like of the resist pattern can be inhibited, leading to a precise pattern transfer. Therefore, the embodiments of the present invention can be highly suitably used in manufacture of LSIs in which further progress of miniaturization is expected in the future, in particular, for forming fine contact holes.

Obviously, numerous modifications and variations of the present invention are possible in light of the above teachings. It is therefore to be understood that within the scope of the appended claims, the invention may be practiced otherwise than as specifically described herein.

The invention claimed is:
1. An inorganic film-forming composition, comprising:
a complex that comprises:
   metal atoms;
   at least one bridging ligand; and
   another ligand which is other than the at least one bridging ligand and which is derived from a hydroxy acid ester, a β-diketone, an α-alkyl-substituted acetoacetic acid ester, a β-ketopentanoic acid ester, a benzoylacetic acid ester, a 1,3-acetonedicarboxylic acid diester, a β-dicarboxylic acid ester or a combination thereof; and
a solvent which comprises a monovalent aliphatic alcohol having 4 or more carbon atoms, an alkylene glycol monoalkyl ether having 4 or more carbon atoms, a hydroxy acid ester having 4 or more carbon atoms, a lactone having 4 or more carbon atoms, a monocarboxylic acid ester of an alkylene glycol monoalkyl ether having 6 or more carbon atoms, or a combination thereof,
wherein the at least one bridging ligand comprises a first bridging ligand derived from a compound represented by formula (1):

(1)

wherein in the formula (1),
   $R^1$ represents an organic group having a valency of n;
   X represents —NCO or —NHR$^a$, wherein R$^a$ represents a hydrogen atom or a monovalent organic group; and
   n is an integer of 2 to 4,
   wherein a plurality of Xs are each identical or different, and
wherein an amount of the first bridging ligand is no less than 50 mol % with respect to a total of the at least one bridging ligand.

2. The inorganic film-forming composition according to claim 1, wherein the bridging ligand coordinates so as to link the metal atoms.

3. The inorganic film-forming composition according to claim 1, wherein the metal atoms are atoms from a Group 3 element, a Group 4 element, a Group 5 element, a Group 6 element, a Group 13 element or a combination thereof, and an amount of the metal atoms is no less than 50 mol % with respect to a total of metal atoms and metalloid atoms comprised in the complex.

4. The inorganic film-forming composition according to claim 1, wherein the first bridging ligand and the another ligand account for no less than 50% of coordination sites of the metal atoms.

5. The inorganic film-forming composition according to claim 1, wherein a number average molecular weight of the complex is no less than 300 and no greater than 10,000.

6. The inorganic film-forming composition according to claim 1, wherein an amount of the another ligand with respect to the metal atoms is no less than 10 mol %.

7. The inorganic film-forming composition according to claim 1, further comprising a crosslinking accelerator.

8. A pattern-forming method comprising:
applying the inorganic film-forming composition according to claim 1 directly or indirectly on a substrate to provide an inorganic film on the substrate;
forming a resist pattern directly or indirectly on the inorganic film; and
forming a pattern on the substrate by at least one dry-etching operation using the resist pattern as a mask.

9. The pattern-forming method according to claim 8, further comprising providing a resist underlayer film on the substrate,
wherein in providing the inorganic film, the inorganic film is provided on the resist underlayer film.

10. The pattern-forming method according to claim 8, wherein forming the resist pattern comprises:
providing a resist film directly or indirectly on the inorganic film using a resist composition;
exposing the resist film; and
developing the exposed resist film.

11. The pattern-forming method according to claim 10,
wherein the resist composition comprises a polymer comprising an acid-labile group, and
wherein a developer solution used in developing the exposed resist film comprises an organic solvent, and a negative type resist pattern is formed.

12. The pattern-forming method according to claim 8, wherein forming the resist pattern is conducted by nanoimprint lithography.

13. The pattern-forming method according to claim 8, wherein the metal atoms are atoms from a Group 3 element, a Group 4 element, a Group 5 element, a Group 6 element, a Group 13 element or a combination thereof, and an amount of the metal atoms is no less than 50 mol % with respect to a total of metal atoms and metalloid atoms comprised in the complex.

14. An inorganic film-forming composition, comprising:
a reaction product obtained in a reaction of:
a metal compound that comprises two or more alkoxy ligands;
a compound represented by formula (1); and
a hydroxy acid ester, a β-diketone, an α-alkyl-substituted acetoacetic acid ester, a β-ketopentanoic acid ester, a benzoylacetic acid ester, a 1,3-acetonedicarboxylic acid diester, a β-dicarboxylic acid ester, or a combination thereof; and
a solvent which comprises a monovalent aliphatic alcohol having 4 or more carbon atoms, an alkylene glycol monoalkyl ether having 4 or more carbon atoms, a hydroxy acid ester having 4 or more carbon atoms, a lactone having 4 or more carbon atoms, a monocarboxylic acid ester of an alkylene glycol monoalkyl ether having 6 or more carbon atoms, or a combination thereof, $$R^1\text{---}(X)_n \quad (1)$$

wherein in the formula (1),
$R^1$ represents an organic group having a valency of n;
X represents —NCO or —NHR$^a$, wherein R$^a$ represents a hydrogen atom or a monovalent organic group; and
n is an integer of 2 to 4,
wherein a plurality of Xs are each identical or different, and
wherein in the reaction product, an amount of a bridging ligand derived from the compound represented by formula (1) is no less than 50 mol % with respect to a total of bridging ligands in the reaction product.

15. The inorganic film-forming composition according to claim 14, wherein the reaction is carried out in presence of water in an amount of no greater than 50 mol % with respect to the metal compound.

16. The inorganic film-forming composition according to claim 14, wherein in the reaction product, no less than 50 mol % of the alkoxy ligands comprised in the metal compound are substituted.

17. The inorganic film-forming composition according to claim 14, wherein the metal atoms are atoms from a Group 3 element, a Group 4 element, a Group 5 element, a Group 6 element, a Group 13 element or a combination thereof, and an amount of the metal atoms is no less than 50 mol % with respect to a total of metal atoms and metalloid atoms comprised in the reaction product.

18. A pattern-forming method comprising:
applying the inorganic film-forming composition according to claim 14 directly or indirectly on a substrate to provide an inorganic film on the substrate;
forming a resist pattern directly or indirectly on the inorganic film; and
forming a pattern on the substrate by at least one dry-etching operation using the resist pattern as a mask.

* * * * *